(12) United States Patent
Kerr et al.

(10) Patent No.: US 8,187,273 B2
(45) Date of Patent: May 29, 2012

(54) APPARATUS, SYSTEM, AND METHOD FOR PERFORMING AN ELECTROSURGICAL PROCEDURE

(75) Inventors: Duane E. Kerr, Loveland, CO (US); Peter D. Gadsby, Broomfield, CO (US); Glenn A. Horner, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 420 days.

(21) Appl. No.: 12/437,254

(22) Filed: May 7, 2009

(65) Prior Publication Data
US 2010/0286691 A1 Nov. 11, 2010

(51) Int. Cl.
*A61B 18/18* (2006.01)
(52) U.S. Cl. .......................................................... 606/51
(58) Field of Classification Search .................. 606/50, 606/51, 52, 207, 210, 41, 49
See application file for complete search history.

(56) References Cited

U.S. PATENT DOCUMENTS

| | | |
|---|---|---|
| 4,763,669 A | 8/1988 | Jaeger |
| 5,047,046 A | 9/1991 | Bodoia |
| 5,334,183 A | 8/1994 | Wuchinich |
| 5,509,922 A | 4/1996 | Aranyi et al. |
| 5,585,896 A | 12/1996 | Yamazaki et al. |
| 5,597,107 A | 1/1997 | Knodel et al. |
| 5,601,601 A | 2/1997 | Tal et al. |
| 5,611,813 A | 3/1997 | Lichtman |
| 5,620,459 A | 4/1997 | Lichtman |
| 5,624,452 A | 4/1997 | Yates |
| 5,626,609 A | 5/1997 | Zvenyatsky et al. |
| 5,688,270 A | 11/1997 | Yates et al. |
| 5,693,051 A | 12/1997 | Schulze et al. |
| 5,716,366 A | 2/1998 | Yates |
| 5,797,927 A | 8/1998 | Yoon |
| 5,807,393 A | 9/1998 | Williamson, IV et al. |
| 5,876,401 A | 3/1999 | Schulze et al. |
| 5,954,731 A | 9/1999 | Yoon |
| 6,004,332 A | 12/1999 | Yoon et al. |
| 6,017,358 A | 1/2000 | Yoon et al. |

(Continued)

FOREIGN PATENT DOCUMENTS

CA 2104423 2/2004

(Continued)

OTHER PUBLICATIONS

U.S. Appl. No. 12/176,679, filed Jul. 21, 2008.

(Continued)

*Primary Examiner* — Jackie Ho
*Assistant Examiner* — Imani Hayman

(57) ABSTRACT

The present disclosure provides a bipolar forceps. The bipolar forceps includes a housing having a handle assembly including a movable handle and one or more shafts. An end effector assembly operatively connects to a distal end of the shaft and includes a pair of first and second jaw members. A solenoid is in operative communication with the movable handle and operatively couples to a drive rod operatively coupled to at least one of the first and second jaw members for causing movement thereof. One or both of the first and second jaw members includes one or more teeth configured to engage one or more teeth located on the drive rod such that rotation of the solenoid imparts one of longitudinal and rotational movement of the drive rod such that at least one of the first and second jaw members moves between the open and closed positions.

9 Claims, 6 Drawing Sheets

U.S. PATENT DOCUMENTS

| | | | |
|---|---|---|---|
| 6,024,741 A | 2/2000 | Williamson, IV et al. |
| 6,080,180 A | 6/2000 | Yoon et al. |
| 6,126,665 A | 10/2000 | Yoon |
| 6,214,028 B1 | 4/2001 | Yoon et al. |
| 6,458,130 B1 | 10/2002 | Frazier et al. |
| 6,511,480 B1 | 1/2003 | Tetzlaff et al. |
| 6,821,285 B2 | 11/2004 | Laufer et al. |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,118,570 B2 | 10/2006 | Tetzlaff et al. |
| 7,118,587 B2 | 10/2006 | Dycus et al. |
| 7,131,970 B2 | 11/2006 | Moses et al. |
| 7,131,971 B2 | 11/2006 | Dycus et al. |
| 7,150,097 B2 | 12/2006 | Sremcich et al. |
| 7,156,846 B2 | 1/2007 | Dycus et al. |
| 7,246,734 B2 | 7/2007 | Shelton, IV |
| 7,252,667 B2 | 8/2007 | Moses et al. |
| 7,255,697 B2 | 8/2007 | Dycus et al. |
| 7,384,420 B2 | 6/2008 | Dycus et al. |
| 7,491,201 B2 | 2/2009 | Shields et al. |
| 7,500,975 B2 | 3/2009 | Cunningham et al. |
| 7,540,872 B2 | 6/2009 | Schechter et al. |
| 7,588,565 B2 | 9/2009 | Marchitto et al. |
| 7,597,693 B2 | 10/2009 | Garrison |
| 2002/0188294 A1 | 12/2002 | Couture et al. |
| 2003/0018331 A1 | 1/2003 | Dycus et al. |
| 2003/0109875 A1 | 6/2003 | Tetzlaff et al. |
| 2003/0181910 A1 | 9/2003 | Dycus et al. |
| 2003/0229344 A1 | 12/2003 | Dycus et al. |
| 2003/0236518 A1 | 12/2003 | Marchitto et al. |
| 2004/0082952 A1 | 4/2004 | Dycus et al. |
| 2004/0087943 A1 | 5/2004 | Dycus et al. |
| 2005/0154387 A1 | 7/2005 | Moses et al. |
| 2006/0064085 A1 | 3/2006 | Schechter et al. |
| 2006/0074417 A1 | 4/2006 | Cunningham et al. |
| 2006/0084973 A1 | 4/2006 | Hushka |
| 2006/0129146 A1 | 6/2006 | Dycus et al. |
| 2006/0167452 A1 | 7/2006 | Moses et al. |
| 2006/0259036 A1 | 11/2006 | Tetzlaff et al. |
| 2007/0062017 A1 | 3/2007 | Dycus et al. |
| 2007/0078456 A1 | 4/2007 | Dumbauld et al. |
| 2007/0088356 A1 | 4/2007 | Moses et al. |
| 2007/0106297 A1 | 5/2007 | Dumbauld et al. |
| 2007/0142833 A1* | 6/2007 | Dycus et al. ............ 606/51 |
| 2007/0260242 A1 | 11/2007 | Dycus et al. |
| 2008/0009860 A1 | 1/2008 | Odom |
| 2008/0033428 A1 | 2/2008 | Artale et al. |
| 2009/0012520 A1 | 1/2009 | Hixson et al. |
| 2009/0018535 A1 | 1/2009 | Schechter et al. |
| 2009/0043304 A1 | 2/2009 | Tetzlaff et al. |
| 2009/0149854 A1 | 6/2009 | Cunningham et al. |
| 2009/0157071 A1 | 6/2009 | Wham et al. |
| 2009/0157075 A1* | 6/2009 | Wham et al. ............ 606/40 |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 0584787 A1 | 3/1994 |
| EP | 1159926 | 12/2001 |
| EP | 1486177 | 12/2004 |
| EP | 1532932 | 5/2005 |
| EP | 1535581 | 6/2005 |
| EP | 1301135 | 9/2005 |
| EP | 1609430 | 12/2005 |
| EP | 1642543 | 4/2006 |
| EP | 1645240 | 4/2006 |
| EP | 1810625 | 8/2009 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 94/20025 | 9/1994 |
| WO | WO 00/24330 | 5/2000 |
| WO | WO 00/24331 | 5/2000 |
| WO | WO 00/36986 | 6/2000 |
| WO | WO 01/54604 | 8/2001 |
| WO | WO 02/07627 | 1/2002 |
| WO | WO 02/080793 | 10/2002 |
| WO | WO 2004/073490 | 9/2004 |
| WO | WO 2004/103156 | 12/2004 |
| WO | WO 2005/110264 | 11/2005 |
| WO | WO 2008/045348 | 4/2008 |
| WO | WO 2008/045350 | 4/2008 |

OTHER PUBLICATIONS

U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.

U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics Figo World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.

Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

APPARATUS, SYSTEM, AND METHOD FOR PERFORMING AN ELECTROSURGICAL PROCEDURE

BACKGROUND

1. Technical Field

The present disclosure relates to an apparatus, system, and method for performing an electrosurgical procedure. More particularly, the present disclosure relates to an apparatus, system, and method for performing an electrosurgical procedure that employs an endoscopic or laparoscopic electrosurgical apparatus that includes an end effector assembly configured for use with various size access ports.

2. Description of Related Art

Electrosurgical apparatuses (e.g., electrosurgical forceps) are well known in the medical arts and typically include a handle, a shaft and an end effector assembly operatively coupled to a distal end of the shaft that is configured to manipulate tissue (e.g., grasp and seal tissue). Electrosurgical forceps utilize both mechanical clamping action and electrical energy to effect hemostasis by heating the tissue and blood vessels to coagulate, cauterize, seal, cut, desiccate, and/or fulgurate tissue As an alternative to open electrosurgical forceps for use with open surgical procedures, many modern surgeons use endoseopes and endoscopic electrosurgical apparatus (e.g., endoscopic forceps or laparoseopic forceps) for remotely accessing organs through smaller, puncture-like incisions. As a direct result thereof, patients tend to benefit from less scarring and reduced healing time. Typically, the endoscopic forceps are inserted into the patient through one or more various types of cannulas or access ports (typically having an opening that ranges from about five millimeters to about twelve millimeters) that has been made with a trocar; as can be appreciated, smaller cannulas are usually preferred.

Forceps that are configured for use with small cannulas (e.g., cannulas less than five millimeters) may present design challenges for a manufacturer of surgical instruments.

SUMMARY

As noted above, smaller cannulas or access ports are usually preferred during an endoscopic procedure. However, because of size constraints associated with the cannula or access port, endoscopic forceps that are configured for use with the smaller cannulas may present design challenges for a manufacturer (e.g., designing an end effector assembly of an endoscopic forceps without compromising the integrity and/or functionality thereof).

Therefore, it may prove useful in the relevant arts to provide an endoscopic forceps that includes an end effector assembly that is configured for use with various types of cannulas or access ports including those that are less than five millimeters. With this purpose in mind, the present disclosure provides a bipolar forceps adapted to connect to a source of electrosurgical energy. The bipolar forceps includes a housing having a handle assembly including a movable handle and one or more shafts that extend from the housing that defines a longitudinal axis therethrough. An end effector assembly operatively connects to a distal end of the shaft and includes a pair of first and second jaw members movable from an open spaced apart position to a closed position to grasp tissue. A solenoid is in operative communication with the movable handle and operatively couples to a drive rod that operatively couples to at least one of the first and second jaw members for causing movement thereof. One or both of the first and second jaw members includes one or more teeth configured to engage one or more teeth located on the drive rod such that rotation of the solenoid imparts at least one of longitudinal and rotational movement of the drive rod such that at least one of the first and second jaw members moves from a first position to a second to clamp tissue.

The present disclosure also provides a method for performing an electrosurgical procedure. The method includes the initial step of providing a bipolar forceps adapted to connect to a source of electrosurgical energy. The bipolar forceps includes a housing having a handle assembly including a movable handle and one or more shafts that extend from the housing that defines a longitudinal axis therethrough. An end effector assembly operatively connects to a distal end of the shaft and includes a pair of first and second jaw members movable from an open spaced apart position to a closed position to grasp tissue. A solenoid is in operative communication with the movable handle and operatively couples to a drive rod that operatively couples to at least one of the first and second jaw members for causing movement thereof. One or both of the first and second jaw members includes one or more teeth configured to engage one or more teeth located on the drive rod such that rotation of the solenoid imparts at least one of longitudinal and rotational movement of the drive rod such that at least one of the first and second jaw members moves from a first position to a second to clamp tissue. The method also includes the steps of: positioning tissue between the pair of first and second jaw members; actuating the electromechanical device to move the drive rod causing the first and second jaw members to move towards each other such that tissue is grasped therebetween; and applying electrosurgical energy to the jaw members such that a tissue seal may be effected therebetween.

The present disclosure further provides a system for performing an electrosurgical device. The system includes a bipolar forceps adapted to connect to a source of electrosurgical energy. The bipolar forceps includes a housing having a handle assembly including a movable handle and one or more shafts that extend from the housing that defines a longitudinal axis therethrough. An end effector assembly operatively connects to a distal end of the shaft and includes a pair of first and second jaw members movable from an open spaced apart position to a closed position to grasp tissue. A solenoid is in operative communication with the movable handle and operatively couples to a drive rod that operatively couples to at least one of the first and second jaw members for causing movement thereof. One or both of the first and second jaw members includes one or more teeth configured to engage one or more teeth located on the drive rod such that rotation of the solenoid imparts at least one of longitudinal and rotational movement of the drive rod such that at least one of the first and second jaw members moves from a first position to a second to clamp tissue. The system also includes a control system having one or more algorithms for one of independently controlling and monitoring the delivery of electrosurgical energy from the source of electrosurgical energy to the electromechanical device and a tissue sealing plate on each of the jaw members.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present disclosure includes an electrosurgical apparatus (e.g., endoseopic or laparoseopic forceps) that includes an end effector assembly that includes a jaw assembly operatively coupled to one or more electromechanical drive assemblies for causing movement of the jaw assembly.

Figure 1:
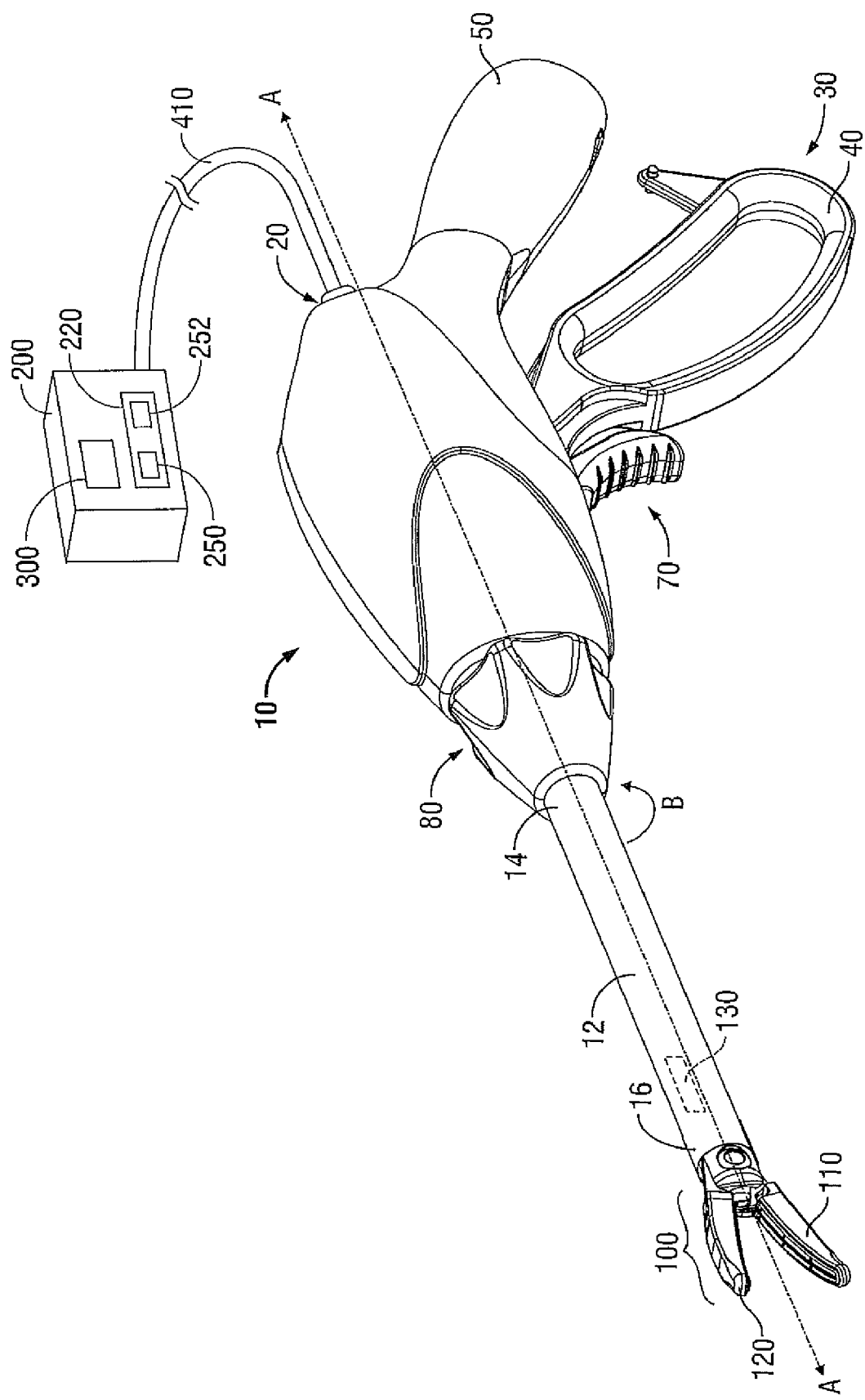
FIG. 1 is a perspective view of an electrosurgical apparatus and electrosurgical generator according to an embodiment of the present disclosure.

With reference to FIG. 1 an illustrative embodiment of an electrosurgical generator 200 (generator 200) is shown. Generator 200 operatively and selectively connects to an endoscopic or laparoscopic forceps (e.g., bipolar forceps 10) for performing an electrosurgical procedure. As noted above, an electrosurgical procedure may include sealing, cutting, cauterizing coagulating, desiccating, and fulgurating tissue; all of which may employ RF energy. Generator 200 may be configured for monopolar and/or bipolar modes of operation. Generator 200 includes all suitable components, parts, and/or members needed for a control system 300 (system 300) to function as intended. Generator 200 generates electrosurgical energy, which may be RE (radio frequency), microwave, ultrasound, infrared, ultraviolet, laser, thermal energy or other suitable electrosurgical energy.

An electrosurgical module 220 generates RF energy and includes a power supply 250 for generating energy and an output stage 252, which modulates the energy that is provided to the delivery device(s), such as the end effector assembly 100, for delivery of the modulated energy to a patient. Power supply 250 may be a high voltage DC or AC power supply for producing electrosurgical current, where control signals generated by the system 300 adjust parameters of the voltage and current output, such as magnitude and frequency. The output stage 252 may modulate the output energy (e.g., via a waveform generator) based on signals generated by the system 300 to adjust waveform parameters, e.g., waveform shape, pulse width, duty cycle, crest factor, and/or repetition rate. System 300 may be coupled to the generator module 220 by connections that may include wired and/or wireless connections for providing the control signals to the generator module 220.

With reference again to FIG. 1, the electrosurgical apparatus can be any suitable type of electrosurgical apparatus, including but not limited to electrosurgical apparatuses that can grasp and/or perform any of the above mentioned electrosurgical procedures. As noted above, one type of electrosurgical apparatus may include bipolar forceps 10 as disclosed in United States Patent Publication No. 2007/0173814 entitled "Vessel Sealer and Divider For Large Tissue Structures". A brief discussion of bipolar forceps 10 and components, parts, and members associated therewith is included herein to provide further detail and to aid in the understanding of the present disclosure.

With continued reference to FIG. 1, bipolar forceps 10 is shown for use with various electrosurgical procedures and generally includes a housing 20, a handle assembly 30 that includes a movable handle 40 and a fixed handle 50, a rotating assembly 80, a trigger assembly 70, a shaft 12, a drive assembly 130, and an end effector assembly 100, which mutually cooperate to grasp, seal and/or divide large tubular vessels and large vascular tissues. Although the majority of the figure drawings depict a bipolar forceps 10 for use in connection with endoscopic or laparoscopic surgical procedures, the present disclosure may be used for more traditional open surgical procedures.

Shaft 12 has a distal end 16 dimensioned to mechanically engage the end effector assembly 100 and a proximal end 14 which mechanically engages the housing 20. In the drawings and in the descriptions that follow, the term "proximal," as is traditional, will refer to the end of the forceps 10 that is closer to the user, while the term "distal" will refer to the end that is farther from the user.

Figure 2:
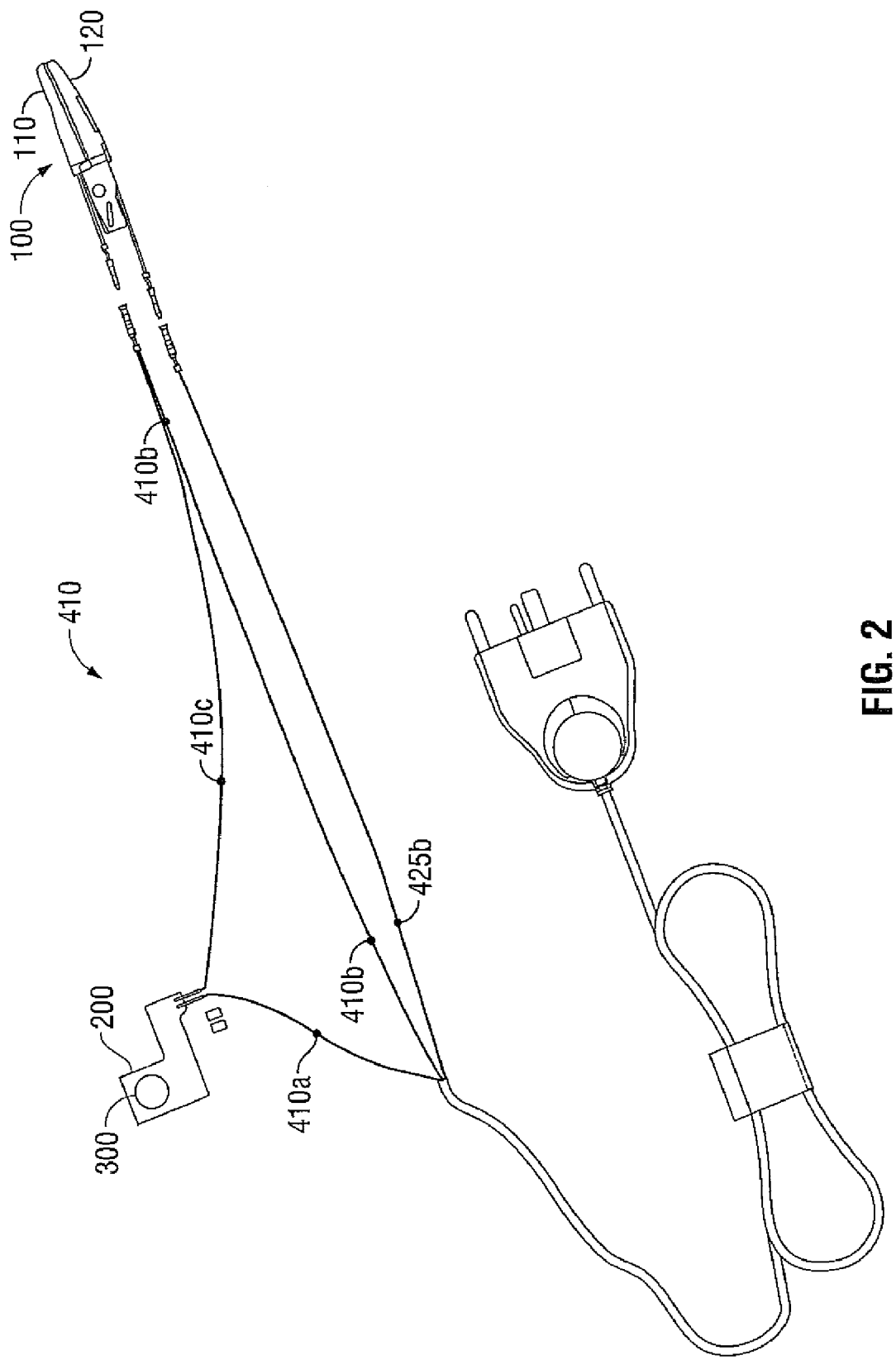
FIG. 2 is a schematic representation of an electrical configuration for connecting the electrosurgical apparatus to the electrosurgical generator depicted in FIG. 1.

Forceps 10 includes an electrosurgical cable 410 that connects the forceps 10 to a source of electrosurgical energy, e.g., generator 200, shown schematically in FIG. 1. As shown in FIG. 2, cable 410 is internally divided into cable leads 410a, 410b, 410c, and 425b which are designed to transmit electrical potentials through their respective feed paths through the forceps 10 to the end effector assembly 100.

For a more detailed description of shaft 12, trigger assembly 70, rotating assembly 80 and electrosurgical cable 410 (including line-feed configurations and/or connections) reference is made to commonly owned Patent Publication No. 2003-0229344, filed on Feb. 20, 2003, entitled "VESSEL SEALER AND DIVIDER AND METHOD OF MANUFACTURING THE SAME."

With reference again to FIG. 1, movable handle 40 includes an aperture configured for receiving one or more of an operator's fingers to enhance movement of the handle 40. Movable handle 40 is in operative communication with generator 200 including system 300, end effector assembly 100 and/or drive assembly 130. Movable handle 40 is selectively, movable from a first position relative to a fixed handle 50 to a second position in closer proximity to the fixed handle 50 to close jaw members 110 and 120. The internal electrically and/or mechanically cooperating components associated with the movable handle 40 to impart movement of the jaw members 110, 120 of end effector assembly 100 is commonly known and may include any number of electrical connections, configurations and/or components (e.g., resistors, capacitors, inductors, rheostats, etc.), and gears, links, springs, and/or rods such that forceps 10 may function as intended.

Fixed handle 50 provides a gripping surface for an operator's hand such that an operator may effectively manipulate the forceps 10 internal or external a patient.

Figure 3:
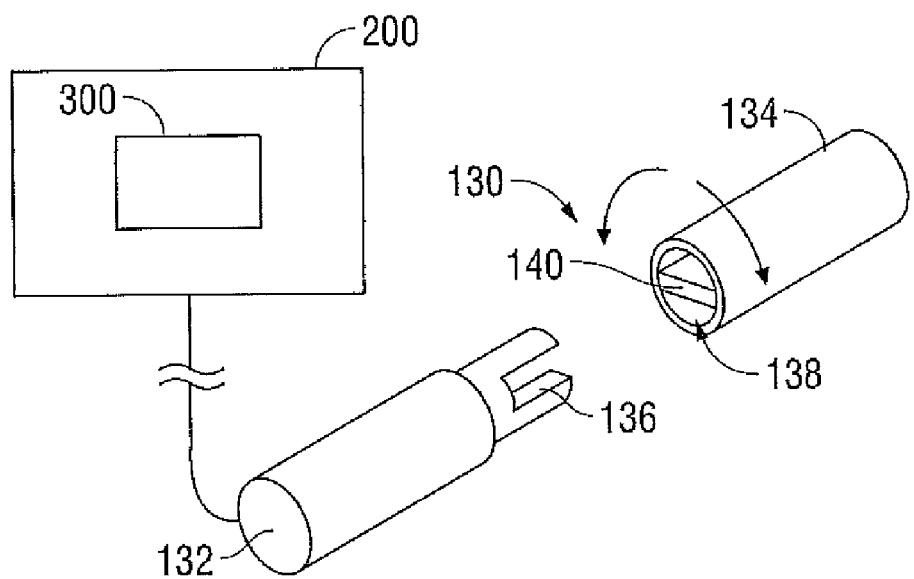
FIG. 3 is an enlarged, side perspective view of a drive assembly suitable for use with the end effector assembly of FIG. 1.

With reference now to FIG. 3, drive assembly 130 is shown. As noted above, drive assembly 130 operatively connects to movable handle 40 such that an operator may impart movement of the jaw members 110, 120. With this purpose in mind, drive assembly 130 may include any number of electrical connections, configurations and/or components (e.g., resistors, capacitors, inductors, rheostats, etc.), and gears, links, springs, and/or rods such that forceps 10 may function as intended. In an embodiment, drive assembly includes a solenoid 132 and a drive rod 134 that operatively couples to one or both of the jaw members 110, 120. While drive assembly 130 is shown including solenoid 132, other electromechanical and/or mechanical devices may be included and/or employed with the drive assembly 130 of the present disclosure, such as, for example, transducers, relays, and the like.

Solenoid 132 may be operatively supported at a distal end of shaft 12 and operatively disposed relative to end effector 100 and/or jaw members 110, 120, such that movement of solenoid 132 causes movement of the jaw members 110, 120. Solenoid 132 serves to convert energy (e.g., electrosurgical energy in the form of an actuation signal) into linear motion, rotational motion, or combination thereof, such that jaw members 110, 120 may move from an opened to closed configuration such that tissue may be grasped therebetween. Solenoid 132 operatively communicates with generator 200 and may include any number of contacts and/or leads. For example, solenoid 132 may include one or more contacts (not explicitly shown) that operatively couple to cable 410. In an embodiment, solenoid 132 may includes a clevis 136 and/or other suitable structure located at a distal end thereof that operatively connects to drive rod 134.

With continued reference to FIG. 3, drive rod 134 is shown. Drive rod 134 is configured to operatively couple to one or both of the jaw members 110, 120 such that one or both of the jaw members 110, 120 is/are moveable from an open configuration to a closed configuration. To this end, drive rod 134 communicates the linear and/or rotational motion produced by solenoid 132 to one or both of the jaw members 110, 120. In an embodiment, drive rod 134 may include and/or define a bore or opening 138, or other suitable structure(s) that couples to clevis 136 of solenoid 132. As shown, opening 138 is defined by drive rod 134 and is generally circumferential in shape and includes a bar or other suitable structure 140 that is configured to engage clevis 136.

Figure 4:
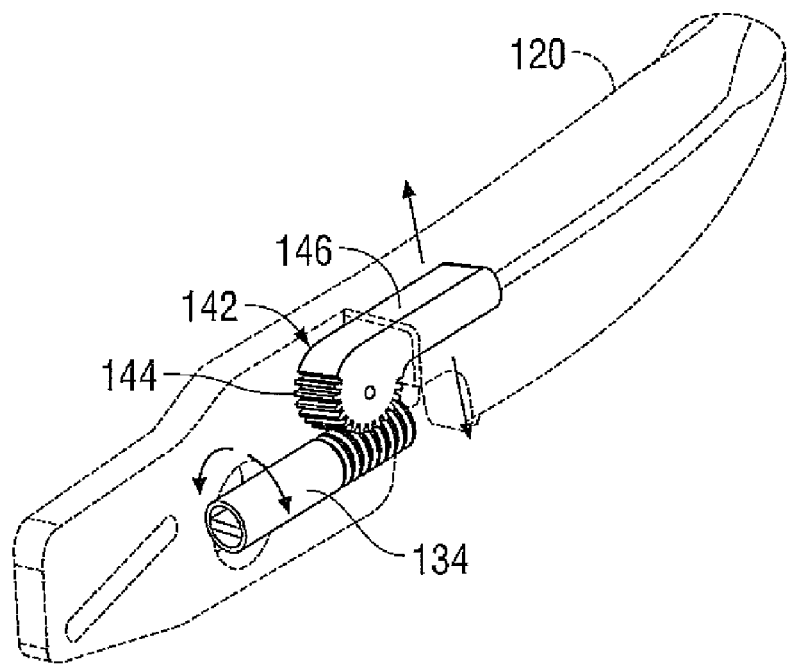
FIG. 4 is an enlarged, side perspective view of a gear configuration suitable for use with the drive assembly of FIG. 4 according to an embodiment of the present disclosure.

Drive rod 134 and one or both of the jaw members 110, 120 may be configured to form a worm gear configuration (FIG. 4). This type of gear configuration is known in the art and typically includes one or more teeth and/or screw-type threads that are configured to matingly engage with each other. While the drive assembly 130 of the present disclosure is described in terms of use with the worm gear configuration, other gear configurations are contemplated, such as, for example, spur gear, single and/or double helical gears, bevel gears, crown gears, hypoid gears, etc.

Depending on a specific gear configuration, opening 138 may be configured to impart linear and/or rotational motion of drive rod 134. For example, in an embodiment that employs a worm gear configuration, opening 138 may be located at a proximal end of drive rod 134. In this instance, rotational movement of the solenoid 132 causes a "worm" (e.g., drive rod 134) to rotate, which, in turn, causes a "gear" (e.g., a gear structure 142 operatively coupled to one or both of the jaw members 110, 120) to rotate and cause one or both of the jaw members 110, 120 to move from an opened to closed configuration. Gear structure 142 includes a proximal end including a plurality of teeth 144 and an elongated distal end 146 configured to operatively couple to one or both of the jaw members 110, 120. For illustrative purposes, gear structure is shown operatively coupled to jaw member 120. As can be appreciated by one of ordinary skill in the art, different gear configurations, which may include more or less of the same, similar, and/or different structures and/or operative connections, may be employed with the drive assembly 130 of the present disclosure.

Figure 5:
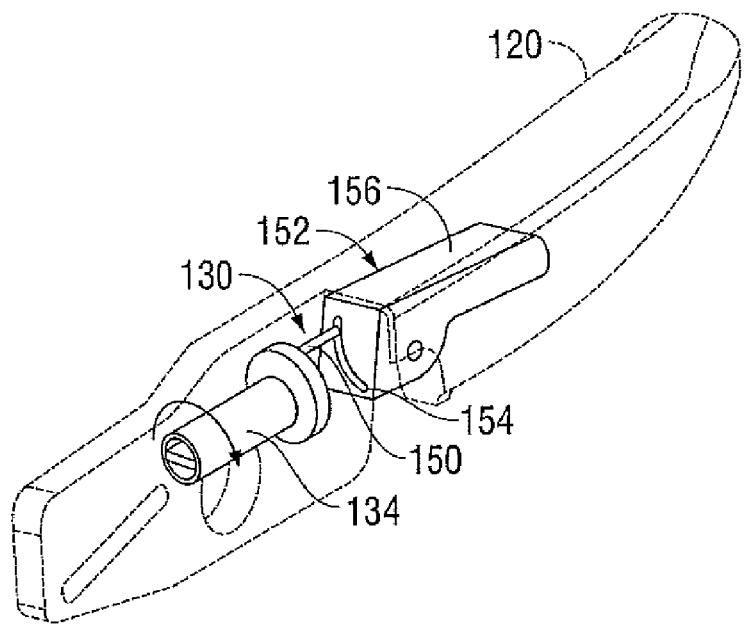
FIG. 5 is an enlarged, side perspective view of an axial cam slot configuration suitable for use with the drive assembly of FIG. 4 according to an embodiment of the present disclosure.

FIG. 5 shows an alternate embodiment of the drive assembly 130. In this instance, the drive rod 134 and one or both of the jaw members 110, 120 form an "axial cam-slot" configuration. More particularly, drive rod 134 includes similar structure (e.g., opening 138 and bar 140) as mentioned above and previously described, and includes one or more rotational cam pins 150 located at a distal end thereof that is configured to engage one or more corresponding cam mechanisms 152 operatively coupled to or defined by one or both of the jaw members 110, 120. Cam mechanism 152 includes a proximal end including one or more cam slots 154 configured to engage cam pin 150 and elongated distal end 156 configured to operatively couple to one or both of the jaw members 110, 120. For illustrative purposes, cam slot structure 152 is shown operatively coupled jaw member 120. In this instance, rotational movement of the solenoid 132 causes cam pin 150 of drive rod 134 to rotate within cam slot 154 on one or both of the jaw members 110, 120, which, in turn, causes one or both of the jaw members 110, 120 to move from an opened to closed configuration. Different camming configurations, which may include more or less of the same, similar, and/or different structures and/or operative connections, may be employed with the drive assembly 130 of the present disclosure.

Figure 6:
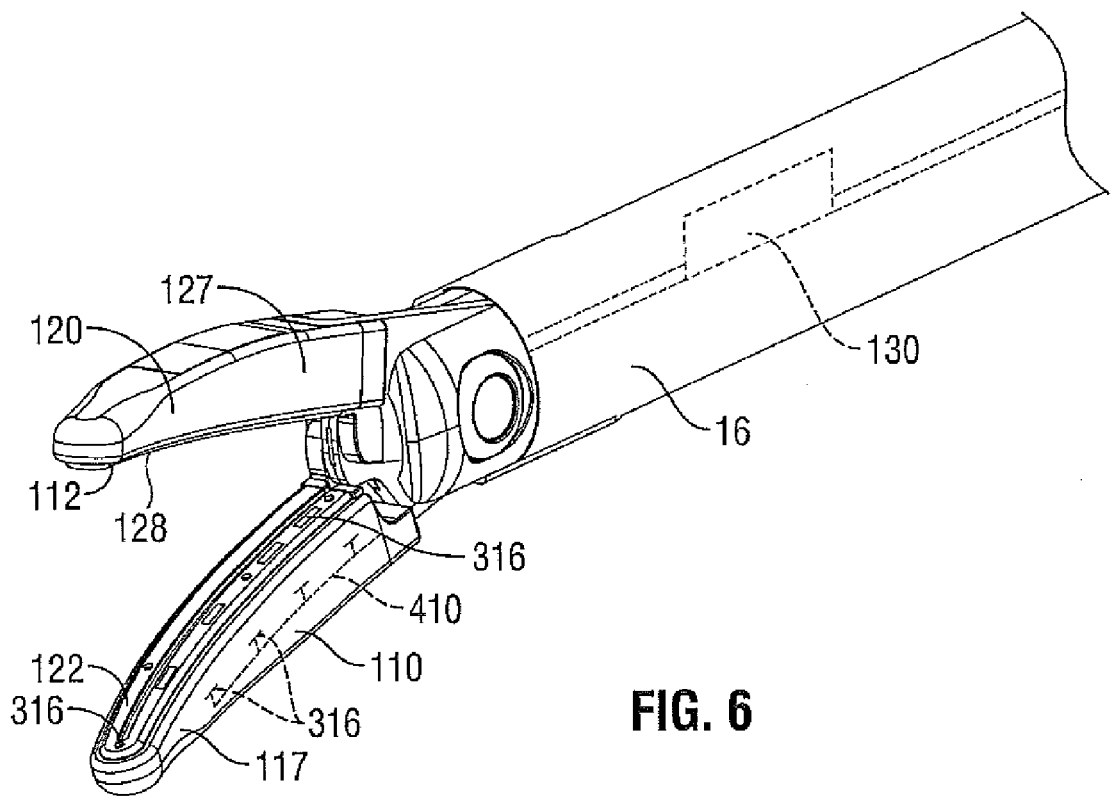
FIG. 6 is an enlarged, side perspective view of the end effector assembly of FIG. 1.

With reference now to FIG. 6 end effector assembly 100 is shown attached at the distal end 16 of shaft 12 and includes a pair of opposing jaw members 110 and 120. As noted above, movable handle 40 of handle assembly 30 operatively couples to drive assembly 130 which, together, electromechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Jaw member 110 includes an insulative jaw housing 117 and an electrically conductive seal plate 118 (seal plate 118). The insulator 117 is configured to securely engage the electrically conductive seal plate 118. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118.

Jaw member 120 includes a similar structure having an outer insulative housing 127 that is overmolded to capture seal plate 128.

As noted above, one or both of the jaw members 110, 120 is/are operatively connected to drive rod 134 of drive assembly 130. In an embodiment, one or both of the jaw members 110, 120 may be operatively connected to one or more gear structures 142 (FIG. 4 illustrates jaw member 120 operatively coupled to gear structure 142) that are configured to mesh with one or more teeth or screw-type threads, such as, for example, those associated with a worm gear configuration. Alternatively, one or both of the jaw members may be operatively coupled to one or more cam mechanism 152 (FIG. 5 illustrates jaw member 120 operatively coupled to cam slot structure 152). In some embodiments, one or both of the jaw members 110, 120, may include openings located at a proximal end thereof and configured to receive one or more of the gear structures 142 and/or cam mechanisms 152.

One or both of the jaw members 110, 120 include one or more sensors 316 (FIG. 6). Sensors 316 are placed at predetermined locations on, in, or along surfaces of the jaw members 110, 120. In some embodiments, end effector assembly 100 and/or jaw members 110 and 120 may have sensors 316 placed near a proximal end and/or near a distal end of jaw members 110 and 120, as well as along the length of Jaw members 110 and 120.

With reference again to FIG. 1, a system 300 for performing an electrosurgical procedure (e.g., RF tissue procedure) is shown. System 300 is configured to, among other things, analyze parameters such as, for example, power, temperature, pressure, current, voltage, impedance, etc., such that a proper tissue effect can be achieved.

Figure 7:
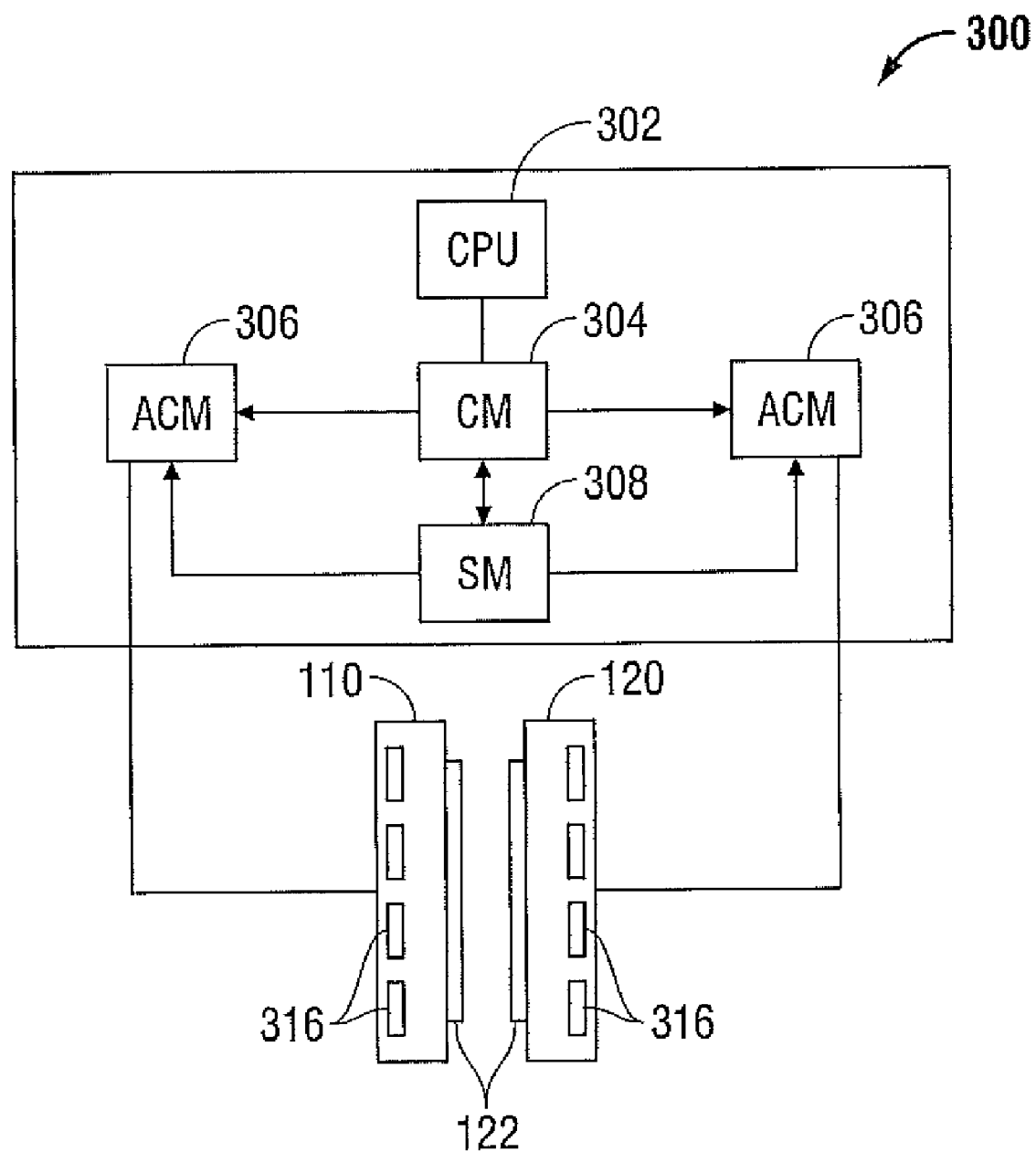
FIG. 7 is a block diagram illustrating components of a control system configured for use with the electrosurgical apparatus and electrosurgical generator of FIG. 1.

With reference now to FIG. 7, system 300 includes one or more processors 302 in operative communication with a control module 304 executable on the processor 302, and may be configured to quantify one or more various parameters (e.g., electrical and/or mechanical parameters associated with bipolar forceps 10) such that a consistent and effective tissue effect may be achieved. Control module 304 instructs one or more modules to transmit electrosurgical energy, which may be in the form of a wave or signal/pulse, via one or more cables (e.g., cable 410) to one or both seal plates 118, 128 and/or an electromechanical drive assembly 130 (drive assembly 130). Control module 304 may instruct an actuation control module 306 (ACM 306) to transmit electrosurgical energy in the form of an actuation signal, via one or more cables (e.g., cable 410) to drive assembly 130.

The control module 304 processes information and/or signals (e.g., pressure data from sensors 316) input to the processor 302 and generates control signals for modulating the electrosurgical energy in accordance with the input information and/or signals. Information may include pre-surgical data (e.g., pressure threshold values) entered prior to the electrosurgical procedure or information entered and/or obtained during the electrosurgical procedure through one or more modules (e.g., ACM 306) and/or other suitable device(s). The information may include requests, instructions, ideal mapping(s) (e.g., look-up-tables, continuous mappings, etc.), sensed information and/or mode selection.

The control module 304 regulates the generator 200 (e.g., the power supply 250 and/or the output stage 252) which adjusts various parameters (e.g., voltage, current, resistance, etc.). Control module 304 may also regulate the electrosurgical energy delivered to the patient (via one or both of the seal plates) and/or to the drive assembly 130 during the electrosurgical procedure.

The control module 304 includes software instructions executable by the processor 302 for processing algorithms and/or data received by sensors 316, and for outputting control signals to the generator module 220 and/or other modules. The software instructions may be stored in a storage medium such as a memory internal to the processor 302 and/or a memory accessible by the processor 302, such as an external memory, e.g., an external hard drive, floppy diskette, CD-ROM, etc.

In some embodiments, an audio or visual feedback monitor or indicator (not explicitly shown) may be employed to convey information to the surgeon regarding the status of a component of the electrosurgical system or the electrosurgical procedure (e.g., pressure excited by the jaw members on tissue grasped therebetween). Control signals provided to the generator module 220 are determined by processing (e.g., performing algorithms), which may include using information and/or signals provided by sensors 316.

The control module 304 regulates the electrosurgical energy in response to feedback information (e.g., information related to tissue condition at or proximate the surgical site and/or information related to jaw operation). Processing of the feedback information may include determining: changes in the feedback information; rate of change of the feedback information; and/or relativity of the feedback information to corresponding values sensed prior to starting the procedure (pre-surgical values) in accordance with the mode, control variable(s) and ideal curve(s) selected. The control module 304 then sends control signals to the generator module 220 such as for regulating the power supply 250 and/or the output stage 252.

Regulation of certain parameters of the electrosurgical energy may be based on a tissue response such as recognition of when a proper seal is achieved and/or when a predetermined threshold temperature value is achieved. Recognition of the event may automatically switch the generator 200 to a different mode of operation and subsequently switch the generator 200 back to an original mode after the event has occurred. In embodiments, recognition of the event may automatically switch the generator 200 to a different mode of operation and subsequently shutoff the generator 200.

ACM 306 (shown as two modules for illustrative purposes) may be digital and/or analog circuitry that can receive instructions from and provide status to a processor 302 (via, for example, a digital-to-analog or analog-to-digital converter). ACM 306 is also coupled to control module 304 to receive one or more electrosurgical energy waves at a frequency and amplitude specified by the processor 302, and/or transmit the electrosurgical energy waves along the cable 410 to one or both of the seal plates 118, 128, drive assembly 130, and/or sensors 316. ACM 306 can also amplify, filter, and digitally sample return signals received by sensors 316 and transmitted along cable 410.

A sensor module 308 senses electromagnetic, electrical, and/or physical parameters or properties at the operating site and communicates with the control module 304 and/or ACM 306 to regulate the output electrosurgical energy. The sensor module 308 may be configured to measure, e.g., "sense", various electromagnetic, electrical, physical, and/or electro-mechanical conditions, such as at or proximate the operating site, including: tissue impedance, tissue temperature, tissue pressure (i.e., pressure exerted by the jaw members on tissue), and so on. For example, sensors of the sensor module 308 may include sensors 316 and/or other suitable sensor(s), such as, for example, optical sensor(s), proximity sensor(s), tissue moisture sensor(s), temperature sensor(s), and/or real-time and RMS current and voltage sensing systems. The sensor module 308 measures one or more of these conditions continuously or in real-time such that the control module 304 can continually modulate the electrosurgical output in real-time.

In some embodiments, sensors 316 may include a smart sensor assembly (e.g., a smart sensor, smart circuit, computer, and/or feedback loop, etc. (not explicitly shown)). For example, the smart sensor may include a feedback loop which indicates when a tissue seal is complete based upon one or more of the following parameters: tissue temperature, tissue pressure, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal.

Operation of bipolar forceps 10 under the control of system 300 is now described. Initially the jaw members 110, 120 are in an open configuration and tissue is positioned therebetween. An operator squeezes movable handle 40 in a direction toward fixed handle 50. Processor 302 instructs ACM 306 to generate electrosurgical energy (e.g., in the form of an actuation signal) in response to the processor instructions. The ACM 306 can access a pulse rate frequency clock associated with a time source (not explicitly shown) to form an electrosurgical pulse/signal (e.g., actuation signal) exhibiting the attributes (e.g., amplitude and frequency) specified by the processor 302 and can transmit such pulse/signal on one or more cables (e.g., cable 410) to drive assembly 130, sensors 316, and/or one or more contacts (not explicitly shown) of solenoid 132. In another embodiment, the processor does not specify attributes of the electrosurgical pulse/signal, but rather instructs/triggers other circuitry to form the electrosurgical pulse/signal and/or performs timing measurements on signals conditioned and/or filtered by other circuitry.

Solenoid 132 converts a portion of the electrosurgical energy of the actuation signal to rotational motion, which, in turn, causes rotation of drive rod 134 of drive assembly 130. Rotation of drive rod 134 imparts movement on one or both of the jaw members 110, 120 such that tissue may be grasped therebetween.

Data, such as, for example, pressure, temperature, impedance and so forth is sensed by sensors 316 and transmitted to and sampled by the ACM 306 and/or sensor module 308.

The data can be processed by the processor 302 and/or ACM 306 to determine, for example, when a threshold pressure (e.g., pressure exerted on tissue by the jaw members 110, 120) value has been achieved. The processor 302 can subsequently transmit and/or otherwise communicate the data to the control module 304 such that output power from generator 200 may be adjusted accordingly. The processor 302 can also subsequently transmit and/or otherwise communicate the data to a local digital data processing device, a remote digital data processing device, an LED display, a computer program, and/or to any other type of entity (none of which being explicitly shown) capable of receiving the such data.

Upon reaching a desired threshold pressure, processor 302 instructs control module 304 to generate electrosurgical energy in response to the processor instructions, to one or more of the seal plates 118, 128 such that a desired tissue effect maybe achieved (e.g., tissue seal).

Once the desired tissue effect has been achieved an operator may release moveable handle 40, which, in turn, causes the jaw members 110, 120 to return to their initial open configuration.

From the foregoing and with reference to the various figure drawings, those skilled in the art will appreciate that certain modifications can also be made to the present disclosure without departing from the scope of the same. For example, instead of employing a drive assembly 130, a solenoid 132 may be directly connected to one or both of the jaw members and configured for imparting movement of one or both of the jaw members. Additionally, solenoid 132 may be in the form of a "pancake motor" and may disposed adjacent to or coupled to a pivot associated with the jaw members 110, 120.

Figure 8:
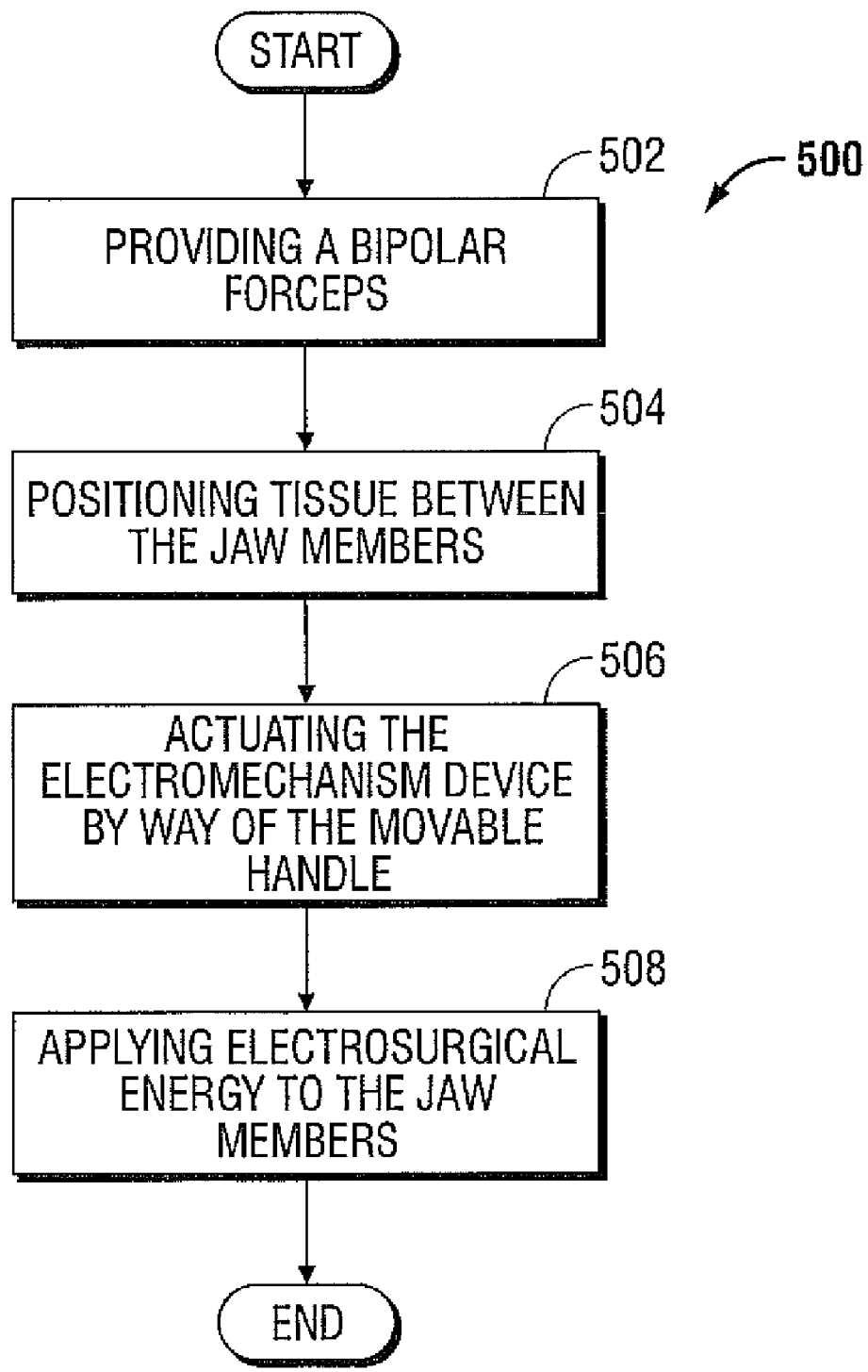
FIG. 8 is a flowchart of a method for performing an electrosurgical procedure according to an embodiment of the present disclosure.

FIG. 8 shows a method 500 for performing an electrosurgical procedure. At step 502, an electrosurgical apparatus e.g. forceps 10 including a pair of jaw members 110, 120 configured to grasp tissue therebetween is provided. At step 504, tissue is positioned between the jaw members 110, 120. At step 506, the electromechanical apparatus is actuated. And at step 508, electrosurgical energy is applied to the jaw members 110, 120 such that a tissue seal may be effected therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps, comprising:
a housing having a handle assembly including a movable handle and at least one shaft that extends from the housing that defines a longitudinal axis therethrough;
an end effector assembly operatively connected to a distal end of the shaft and includes a pair of first and second jaw members, at least one of which is movable to move the first and second jaw members from an open position to a closed position to grasp tissue; and
a solenoid in operative communication with the movable handle and operatively coupled to a drive rod that operatively couples to at least one of the first and second jaw members for causing movement thereof,
wherein at least one of the first and second jaw members includes one or more teeth configured to engage one or more teeth located on the drive rod such that rotation of the solenoid imparts at least one of longitudinal and rotational movement of the drive rod, thereby moving the first and second jaw members between the open and closed positions.

2. The bipolar forceps according to claim 1, wherein at least one of the first and second jaw members includes at least one cam slot configured to engage at least one cam pin located on the drive rod.

3. The bipolar forceps according to claim 1, wherein the solenoid is located adjacent the end effector assembly.

4. The bipolar forceps according to claim 1, wherein the solenoid is housed within at least one of the jaw members.

5. The bipolar forceps according to claim 1, wherein the bipolar forceps is in operative communication with a control system operatively coupled to a source of electrosurgical energy and is configured for generating an actuation signal for driving the drive assembly.

6. A method for performing an electrosurgical procedure, the method comprising:
providing a bipolar forceps including:
a housing having a handle assembly including a movable handle and at least one shaft that extends from the housing that defines a longitudinal axis therethrough;
an end effector assembly operatively connected to a distal end of the shaft and includes a pair of first and second jaw members movable from an open spaced apart position to a closed position to grasp tissue; and
a solenoid in operative communication with the movable handle and operatively coupled to a drive rod that operatively couples to at least one of the first and second jaw members for causing movement thereof,
wherein at least one of the first and second jaw members includes one or more teeth configured to engage one or more teeth located on the drive rod such that rotation of the solenoid imparts at least one of longitudinal and rotational movement of the drive rod such that at least one of the first and second jaw members moves between the open and closed positions;
positioning tissue between the pair of first and second jaw members;

actuating the solenoid by way of the movable handle to move the drive rod that causes the first and second jaw members to move towards each other such that tissue is grasped therebetween; and applying electrosurgical energy to the jaw members such that a tissue seal may be effected therebetween.

7. The method according to claim 6, wherein the step of actuating further includes the step of measuring a pressure exerted on tissue by the jaw members.

8. The method according to claim 6, further comprising independently controlling and monitoring the delivery of electrosurgical energy.

9. A system for performing an electrosurgical procedure comprising:

a bipolar forceps including:

a housing having a handle assembly including a movable handle and at least one shaft that extends from the housing that defines a longitudinal axis therethrough;

an end effector assembly operatively connected to a distal end of the shaft and includes a pair of first and second jaw members movable from an open spaced apart position to a closed position to grasp tissue;

a solenoid in operative communication with the movable handle and operatively coupled to a drive rod that operatively couples to at least one of the first and second jaw members for causing movement thereof, wherein at least one of the first and second jaw members includes one or more teeth configured to engage one or more teeth located on the drive rod such that rotation of the solenoid imparts at least one of longitudinal and rotational movement of the drive rod such that at least one of the first and second jaw members moves between the open and closed positions; and wherein the bipolar forceps is in operative communication with a control system having at least one algorithm for at least one of independently controlling and monitoring the delivery of electrosurgical energy from a source of electrosurgical energy to the solenoid and the tissue sealing plate on each of the jaw members.

\* \* \* \* \*